United States Patent
Dong et al.

(10) Patent No.: US 7,034,161 B2
(45) Date of Patent: Apr. 25, 2006

(54) PROCESS FOR PRODUCING A RIBOFURANOSE

(75) Inventors: Zhiming Dong, Florence, SC (US); Pingsheng Zhang, Florence, SC (US)

(73) Assignee: Hoffmann-La Roche Inc., Nutley, NJ (US)

( * ) Notice: Subject to any disclaimer, the term of this patent is extended or adjusted under 35 U.S.C. 154(b) by 29 days.

(21) Appl. No.: 10/638,740

(22) Filed: Aug. 11, 2003

(65) Prior Publication Data

US 2004/0034213 A1 Feb. 19, 2004

Related U.S. Application Data

(60) Provisional application No. 60/402,780, filed on Aug. 12, 2002.

(51) Int. Cl.
*C07D 249/08* (2006.01)

(52) U.S. Cl. .................. 548/266.8; 548/262.2
(58) Field of Classification Search ................. 549/475; 548/262.2, 266.8
See application file for complete search history.

(56) References Cited

U.S. PATENT DOCUMENTS 4,914,233 A * 4/1990 Freskos et al. .......... 536/27.11
6,130,326 A * 10/2000 Ramasamy et al. ........ 536/28.7
6,518,253 B1 * 2/2003 Tam .............................. 514/42
6,660,854 B1 * 12/2003 Lee et al. .................. 536/55.3

FOREIGN PATENT DOCUMENTS

| WO | WO 01/46212 | * 12/2000 |
| WO | WO 01/46212 | * 6/2001 |
| WO | WO 03 011883 | 2/2003 |

OTHER PUBLICATIONS

Basic Nucleic Acid Chemistry: vol. 1, Paul T'so, (ED) 1975, pp. 116–125.*

Guthrie et al., Chem. Ind., pp. 547–548 (1968.

Ramasamy et al., J. Med. Chem., 43, pp. 1019–1028 (2000).

* cited by examiner

Primary Examiner—Golam M. M. Shameem
(74) Attorney, Agent, or Firm—George W. Johnston; Patricia S. Rocha-Tramaloni

(57) ABSTRACT

A method of converting pure α-anomer or β/α-anomer mixtures of 1,2,3,5-tetra-O-acetyl-L-ribofuranose to methyl-1-(2,3,5-tri-O-acetyl-β-L-ribofuranosyl)-1,2,4-triazole-3-carboxylate an intermediate for levovirin, as well as, the novel pure α-anomer, alpha 1,2,3,5-tetra-O-acetyl-L-ribofuiranose, are useful in manufacturing levovirin.

6 Claims, No Drawings

PROCESS FOR PRODUCING A RIBOFURANOSE

PRIORITY TO PROVISIONAL APPLICATION(s) UNDER 35 U.S.C. §119(e)

This application claims priority under 35 U.S.C. §119(e) of provisional application(s) Ser. No. 60/402,780, filed on Aug. 12, 2002.

BACKGROUND OF THE INVENTION

The compound, levovirin, is a known antiviral agent having the formula:

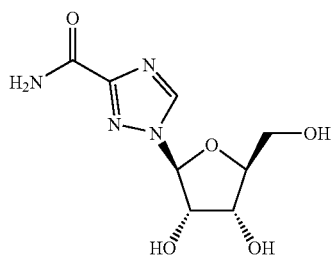

I

Levovirin has been produced from β-tetraacetyl-L-ribofuranose, the β-anomer of a compound of the formula:

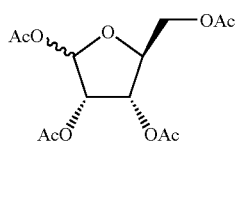

1,2,3,5-tetra-O-acetyl-L-ribofuranose

II

In accordance with prior procedures, the β-anomer of the compound of Formula II, i.e., the compound of Formula II-A, is converted to levovirin by the following reaction scheme:

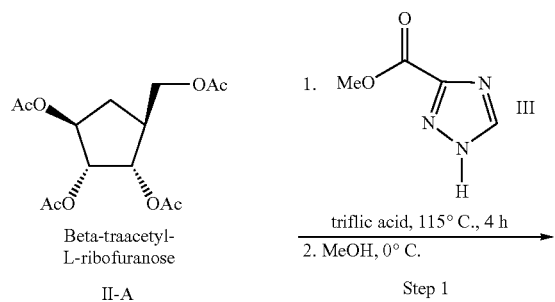

Beta-traacetyl-L-ribofuranose

II-A

Step 1 triflic acid, 115° C., 4 h
2. MeOH, 0° C.

[continues with L-Ribomethylester IV, Step 2 (1. 4 eq. NH3 MeOH, 25–35° C.; 2. Cryst. from MeOH), Crude Levovirin I, Step 3 (Recrystallization from aq. EtOH), Levovirin I]

In this reaction scheme, the pure β-tetraacetyl-L-ribofuranose (the compound of Formula II-A) is used as the starting material. Although pure β-tetraacetyl-L-ribofuranose is commercially available, its price is high. Therefore, the cost of levovirin produced by this method has been expensive. In view of the fact that the compound of Formula II-A is difficult to produce inexpensively, this also has been a major problem with this synthesis.

As disclosed in Ramasamy, Tam, et al., *J. Med. Chem.*, 43:1019 (2000), the compound of Formula II-A has been produced from L-ribose which has the formula:

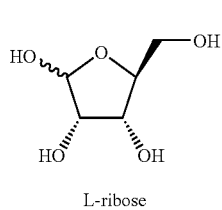

L-ribose

V

This synthesis has involved eight evaporation to dryness steps and sixteen extraction operations to produce the compound of Formula II-A in pure form for its conversion to the compound Levovirin. This process has not been suitable for scale up.

In 1968, Guthrie and Smith in *Chem., Ind.*, 547–548 (1968) proposed a method for converting D-ribose into β-tetra-O-acetyl-D-ribofuranose, an enantiomer of the compound of Formula II-A. This method contained three chemical transformations, the acetal formation, acetylation, and acetolysis. Ramasamy et al's synthesis followed Guthrie's synthetic strategy in which the acetal formation was effected in MeOH and HCl, the acetylation was carried out with acetic anhydride in pyridine, and the acetolysis was conducted in acetic acid and acetic anhydride in the presence of concentrated sulfuric acid. The crude product was a mixture of α/β-anomers of tetra-O-acetyl-L-ribofuranose and the pure β-anomer of tetra-O-acetyl-L-ribofuranose was obtained in 57% overall yield via recrystallization from ethyl ether.

This cumbersome procedure producing poor yields was considered necessary since it was believed that only the β-anomer of Formula II-A could be used in the synthesis of levovirin of Formula I. Therefore, in this procedure, the compound of Formula II-A had to be purified and separated from its α-anomer, the compound of Formula II-B

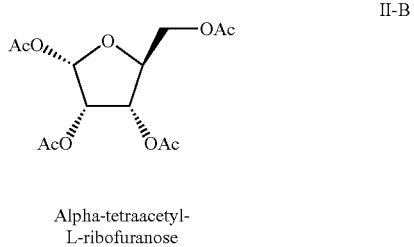

Alpha-tetraacetyl-
L-ribofuranose

Therefore, under the prior procedures, it was believed that it was necessary to separate and remove the compound of Formula II-B from the compound of Formula II in order to carry out this synthesis. This has involved costly separation techniques and led to reduced yields. In summary, these processes have made the production of the compound of Formula I costly.

SUMMARY OF INVENTION

In accordance with this invention, it has been found that α-tetraacetyl-L-ribofuranose of Formula II-B can be converted to the compound of Formula IV which is an intermediate for levovirin. In this manner, any mixture of the compound of Formula II-A and II-B can be converted to levovirin easily without separation. With this discovery, levovirin can be easily and cheaply produced from L-ribose (the compound of Formula V). Because of the fact that the compound of Formula II-B can be converted to the compound of Formula IV, an intermediate for levovirin, the subject invention provides an easy method for preparing the compound of Formula II in high yields, without costly and yield lowering purification and separation techniques. These high yields are translated into the high yields of the compound of Formula I, levovirin.

DETAILED DESCRIPTION

In the diagrams, a bond indicated by a (━◀)) indicates the substituent above the plane of the molecule. On the other hand, a bond indicated by a ((⸱⸱⸱⸱⸱)) indicates that the substituent is below the plane of the molecule. When a ((∿∿)) is used, this indicates that the bond constitutes a mixture of the α- and β-anomers; some above the plane and some below the plane of the molecule.

In accordance with this invention, it has been found that the stereoisomer, the compound of Formula II-B, can be converted directly to the compound of Formula IV in the same manner as the compound of Formula II-A. Therefore, a mixture of the compound of Formula II-A and II-B can be converted to the compound of Formula IV without separation or purification. This opens a new method for preparing the compound of Formula II from L-ribose of Formula V.

In accordance with this invention, the L-ribose is converted to the compound of Formula II by the following reaction scheme:

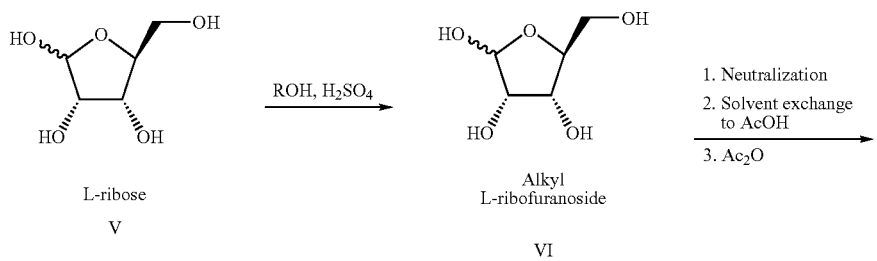

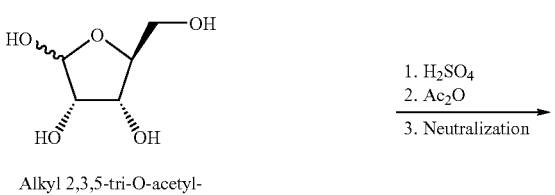

Alkyl 2,3,5-tri-O-acetyl-
L-ribofuranoxide

VII

-continued

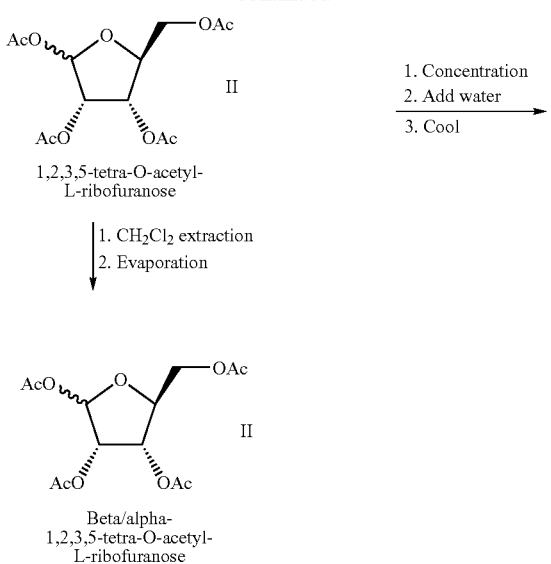

1,2,3,5-tetra-O-acetyl-
L-ribofuranose

1. CH$_2$Cl$_2$ extraction
2. Evaporation

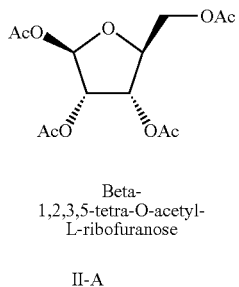

1. Concentration
2. Add water
3. Cool

Beta-
1,2,3,5-tetra-O-acetyl-
L-ribofuranose

II-A

Beta/alpha-
1,2,3,5-tetra-O-acetyl-
L-ribofuranose

Wherein R is lower alkyl

R can be any unsubstituted saturated hydrocarbon lower alkyl radical containing from 1 to 4 carbon atoms such as methyl, ethyl, propyl, isopropyl, etc. It is preferred that R in the above reaction scheme be methyl. The term lower alkanol designates an aliphatic lower alkanol containing from 1 to 4 carbon atoms. Lower alkanols are lower alkyl alcohols, where lower alkyl is defined as above. The preferred lowered alkanol is methanol.

In the first step of the above reaction scheme, the compound of Formula V, i.e., L-ribose, is converted into the acetal of Formula VI. Any conventional method of forming an acetal can be utilized to affect this conversion. Generally, this reaction is carried out by reacting the L-ribose with a lower alkanol, preferably methanol in the presence of an acid, generally a strong inorganic acid. Any conventional, strong, inorganic acid can be utilized such as hydrochloric acid, sulfuric acid, etc. The acid catalyzes the reaction to produce the acetal of Formula VI. Generally, this reaction is carried out in the presence of excess alkanol as the solvent medium. This reaction can be carried out at room temperature and atmospheric pressure. Normally temperatures are from about 0° C. to about 30° C. are utilized with temperatures of from about 18° C. to about 25° C. being preferred.

The conversion of compound V to the compound of Formula VI can be stopped by neutralizing the acid in the reaction medium containing the lower alkanol, which reaction medium was used to produce the acetal of Formula VI. Neutralization is achieved by adding a base to this reaction medium. Any conventional base can be utilized for neutralizing the reaction medium. However, among the preferred bases are the weak inorganic or organic bases, such as alkali metal salts, particularly sodium carbonate, lithium carbonate, and lithium acetate with lithium carbonate and lithium acetate being preferred. Any conventional method of neutralizing the reaction medium to a pH of from 4 to 7, preferably from 5.0 to 6.5 can be utilized to stop this reaction. Therefore, the base should be added until a pH of from 5 to 7 is achieved. After the reaction is stopped the rest of the reactions to produce the compound of Formula II, i.e. acetylation and acetolysis, are carried out in a solvent medium containing acetic acid. It is through the use of a reaction medium containing acetic acid for both acetylation and acetolysis that high yields of the compound of Formula II are obtained. The use of acetic acid as the solvent medium allows simple procedures to produce the compound of Formula II, either as a pure α-anomer, pure β-anomer or as mixture of these anomers. In this manner all the "evaporation to dryness" and extraction operations used in the previous methods are eliminated and the overall operation is greatly simplified.

In order to utilize acetic acid as the solvent medium in the production of the compound of Formula VII from the compound of Formula VI, the lower alkanol solvent in the reaction medium is removed and replaced by acetic acid. The solvent exchange is accomplished by replacing the lower alkanol with acetic acid. Any conventional method of removing the methanol from the reaction mixture which produces the compound of Formula VI can be utilized. This can be accomplished by distilling off the methanol from the reaction medium and thereafter adding acetic acid. In the acetic acid solvent medium, the compound of Formula VI is converted to the compound of Formula VII by the addition of acetic anhydride. In carrying out this reaction temperatures of from about 60° C. to 110° C. are generally utilized with temperatures of from about 90° C. to 105° C. being especially preferred. This reaction is carried out for a period of time sufficient to produce the triacetate of Formula VII.

The triacetate compound of Formula VII in the acetic acid reaction medium can be directly converted to the tetraacetate compound of Formula II by acetolysis utilizing a strong acid such as sulfuric acid. While sulfuric acid is exemplified, any strong acid can be utilized to carry out this reaction such as the strong inorganic acids which include hydrochloric and hydrobromic acid. This acetolysis reaction occurs via the elimination of the alkoxy group (such as methoxy) and the subsequent addition of acetyloxy group to produce the compound of Formula II. The acetolysis reaction is reversible and the reaction is driven to completion by the consumption of methanol with acetic anhydride. The use of acetic anhydride in an acid reaction medium accomplishes the conversion to the compound of Formula II in a single reaction medium without extensive isolation steps. In carrying out this reaction, temperature and pressure are not critical and this reaction can be carried out at room temperature and atmospheric pressure. In carrying out this reaction, temperatures of from about 0° C. to 30° C. are generally utilized with temperatures of from about 18° C. to 25° C. being preferred.

The conversion of the compound of Formula VI to the compound of Formula II can be carried out in a single reaction medium without changing solvents or materials by the simple addition of acetic anhydride followed by the addition of a strong mineral acid to produce the compound of Formula II. The acetolysis reaction medium in which the compound of Formula II is formed is then neutralized to stop the reaction in the same way described hereinbefore in connection with the reaction medium in which the compound of Formula VI is produced.

The compound of Formula II thus produced which consists of the α- and β-anomers can be utilized in the conversion of the compound of Formula II to the compound of Formula IV by reaction with triazolemethylester of Formula III. This conversion is carried out at a temperature from about 90° C. to about 130° C. In accordance with this invention both the α- and β-anomers are converted, by reaction with the compound of Formula III, to the compound of Formula IV having the β configuration with respect to the triazolemethylester portion of this molecule.

If it is desired to isolate the β-anomer of Formula II-A from the mixture of Formula II produced in the acetolysis reaction, this can be done by adding water to the reaction mixture and cooling the reaction mixture to a temperature of from about 0° C. to about 10° C. In this manner the compound of Formula II-A, in its pure form, is produced in accordance with this invention, by simply adding water to the reaction mixture in which the compound of Formula II is formed and upon cooling to the aforementioned temperatures, the compound of Formula II-A precipitates. In this manner a simple procedure is provided for isolating the compound of Formula II-A in pure form without the presence of the other anomer of Formula II-B. If one wishes to obtain the compound of Formula II-B, this is done after the compound of Formula II-A is separated out of the reaction medium by extracting the mixture of compounds of Formula II-A/B from the reaction medium and a subsequent isolation of the compound of Formula II-B in pure form from this mixture via column chromatography. Any conventional method of extracting the compounds of Formula II-A/B from the reaction mixture can be carried out such as by utilizing a low boiling organic solvent such as a halogenated carbon, ester, and ether, or their combinations. Any conventional method of isolating the compound of Formula II-B by column chromatography can be carried out such as by using silica gel and eluting with a combination of low boiling organic solvents. In this manner pure compound of Formula II-B can be obtained without the presence of its anomer of Formula II-A.

In accordance with this invention, the compound of Formula II need not be separated into its anomers for conversion to levovirin. The mixture of the compounds Formula II-A and II-B can be directly converted without separation of anomers to the compound of Formula IV by reaction with the compound of Formula III in the aforementioned manner to produce the desired configuration of the compound of Formula IV so that it can be converted to levovirin.

In accordance with this invention any mixture of anomers of the compound of Formula II can be converted directly to the compound of Formula IV. The conversion of Formula V to the compound of Formula II, in accordance with the above scheme can produce the compound of Formula II as a mixture containing at least ten mole percent (10 mole %) of the α-anomer and at most ninety mole percent (90 mole %) of the β-anomer depending upon the reaction conditions. Therefore, in accordance with this invention any mixture of anomers, even those containing as little as ten mole percent (10 mole %) of the α-anomer and at most ninety mole percent (90 mole %) of the β-anomer or even one hundred mole percent (100 mole %) of the α-anomer can be converted to the compound of Formula IV. As is set forth in accordance with this invention, the pure α-anomer can be converted to the compound of Formula IV.

As seen from the above, there is a great advantage of the process of this invention since a mixture of α/β-tetra-O-acetyl-L-ribofuranoses can be used to prepare levovirin. In the existing processes, pure β-tetra-O-acetyl-L-ribofuranose was only used to prepare the compound of Formula IV. The conversion of L-ribose to the tetraacetate of Formula II produces a molar mixture of β/α-anomers usually ranging from 2:1 to 3:1. If only the β-anomer is utilized, at least 25% of the products are wasted. In addition, there will be some β-anomer losses during its isolation (crystallization). L-ribose is a fairly expensive material.

In the examples, EtOAc is ethyl acetate and TBME is tertiary butyl methyl ether. All of the solvent ratios are designated as parts by volume. The ratio of α/β is given as a mole ratio. Hence a 3:1 mixture of α/β is 3 moles of the α-anomer per mole of the β-anomer in the mixture.

EXAMPLE 1

Preparation of dichloromethane solution of crude—β/α-1,2,3,5-tetra-O-acetyl-L-ribofuranose

| | Preparation of dichloromethane solution of crude-β/α-1,2,3,5-tetra-O-acetyl-L-ribofuranose |
|---|---|
| 100 g | A dry, clean 1 L 4-neck round bottom flask was charged with of L-ribose and |
| 500 mL | of methanol. The mixture was stirred at 20° C. while |
| 9.6 g | of 95% sulfuric acid was slowly added. After the addition the mixture was stirred at 20° C. for 3 h to complete the transformation of L-ribose to Methyl L-ribofuranoside. To this reaction mixture was slowly added |
| 11.7 g | of lithium carbonate. The mixture was stirred for 30 minutes. Methanol (320 g) was distilled out under reduced pressure (bath temperature: 45° C.) To the mixture was added |
| 360 g | of acetic acid. The distillation was continued until 340 g liquid was distilled out (high vacuum, bath temperature: 63° C., pot temperature should be controlled, not to exceed 52° C.). The bath temperature was lowered to 50° C. and |
| 251.6 g | of acetic anhydride was added. After the addition the mixture was held for 1 h and then heated to 100° C. and held for 4 h to complete the formation of methyl 2,3,5-tri-O-acetyl-L-ribofuranoside. The mixture was then cooled to 20 ± 5° C. (pot temperature) and |
| 52.6 g | of 95% sulfuric acid was slowly added. The addition rate should be controlled so as to ensure the at the pot temperature is 20 ± 5° C. After the completion of the addition the mixture was stirred for 30 min at 20 ± 5° C. Then, |
| 95.2 g | of acetic anhydride was slowly added in 2 hr while maintaining the pot temperature at 20 ± 5° C. After the addition the mixture was stirred at 20 ± 5° C. (pot temperature) for 30 minutes to finish the tranformation to beta-/alpha-1,2,3,5-tetra-O-acetyl-L-ribofuranoses. The mixture was neutralized with |
| 52.1 g | of lithium carbonate and then was concentrated under reduced pressure until over 419 mL of liquid was distilled out (vacuum: 60 mbar, bath temperature: 60° C., final pot temperature: 57° C.). The mixture was cooled to 25 ± 5° C. and to it was added |
| 150 mL | of dichloromethane and |
| 400 mL | of water. The mixture was stirred at moderate speed for 30 minutes. The stirring was stopped and the mixture was held still for 15 min. The organic phase was separated. To the aqueous layer in the pot was added another |
| 150 mL | of dichloromethane. The mixture was stirred at moderate speed for 15 minutes and then held still for 15 min. The organic phase was separated. Both organic layers were combined and washed with |

| continued | |
|---|---|
| Preparation of dichloromethane solution of crude-β/α-1,2,3,5-tetra-O-acetyl-L-ribofuranose | |
| 160 mL | of 4% sulfuric acid. The pH of the aqueous phase should be below 2 at this point. The organic phase was separated as a clear light-yellow solution, which typically contained ~11% of alpha-1,2,3,5-tetra-O-acetyl-L-ribofuranoses and ~27% beta-1,2,3,5-tetra-O-acetyl-L-ribofuranoses. |

EXAMPLE 2

Preparation of methyl 1-(2,3,5-tri-O-acetyl-beta-L-ribofuranosyl)-1,2,4-triazole-3-carboxylate using a Mixture of β/α-1,2,3,5-tetra-O-acetyl-L-ribofuranose

| Preparation of methyl 1-(2,3,5-tri-O-acetyl-beta-L-ribofuranosyl)-1,2,4-triazole-3-carboxylate using a Mixture of β/α-1,2,3,5-tetra-O-acetyl-L-ribofuranose | |
|---|---|
|  | A 2 L flask was charged with |
| 80.5 g | of triazolemethylester, the above dicholomethane solution of β/α-1,2,3,5-tetra-O-acetyl-L-ribofuranose, and |
| 37 g | of acetic anhydride at ambient temperature. The mixture was distilled at atmospheric pressure (bath temperature, 90° C.). When the pot temperature reached 85° C. and the distillation became very slow, vacuum was applied (up tp 30 mbar) and the distillation was continued for 40 minutes at 90° C. (bath temperature, the pot temperature reached 117° C.). The vacuum was released and |
| 843 mg | of triflic acid was slowly added. After the addition the vacuum was restored and the mixture was stirred at 115 ± 5° C. (pot temperature) for 4 h. Upon completion of the reaction the mixture was cooled to 70° C. and to it was added |
| 750 mL | of 2B alcohol (ethyl alcohol). When a homogenous solution was formed the mixture was cooled to 50° C. and held until heavy precipitation formed (seeding might be necessary). The mixture was then slowly cooled to −5° C. (bath temperature) in 2 h and held for at least 2 h. The solid was filtered, washed with |
| 100 mL | of cold 2B Alcohol (ethyl alcohol), and dried under vacuum at 50° C. for 17 h to give 192.7 g (75.1% yield from L-ribose) of methyl 1-(2,3,5-tri-O-acetyl-beta-L-ribofuranosyl)-1,2,4-trizole-3-carboxylate as an off-white solid. |

EXAMPLE 3

| Preparation of pure beta-1,2,3,5-tetra-O-acetyl-L-ribofuranose | |
|---|---|
|  | To a 1 L dry, clean round bottom jacketed flask was added |
| 50.0 g | of L-Ribose and |
| 400 g | of dry Methanol. To this mixture was added |
| 4.60 g | of 95% Sulfuric Acid. After the addition the mixture was stirred at ambient temperature for 3 hr. To the content was added |
| 5.85 g | of Lithium Carbonate in one portion and the mixture was stirred at ambient temperature for 30 min. The mixture was subject to vacuum distillation at bath temperature 30° C. (pot temperature 18° C.) till 320 g methanol was collected. The distillation was stopped and |
| 103 g | of Acetic Acid was added. The vacuum distillation was reassumed (at bath temperature 40° C.) till 89 g distillate was collected. The distillation was again stopped and |
| 146 g | of Acetic Acid was added. Vacuum distillation was reassumed at bath temperature 40° C. and then slowly increased to 50° C. to distill out about 140 g of liquid. To this mixture was added |
| 125.8 g | of Acetic Anhydride. The mixture was heated to ca. 100 ± 5° C. and maintained for 5 ± 1 hr. The mixture was then cooled to 20° C. and to it was slowly added |

| Preparation of pure beta-1,2,3,5-tetra-O-acetyl-L-ribofuranose | |
|---|---|
| 26.3 g | of 95% Sulfuric Acid over 30 min while controlling pot temperature not exceeding 25° C. After the addition the mixture was stirred for 30 min at 20 ± 5° C. |
| 47.6 g | of Acetic Anhydride was added slowly over 2 hrs at 20 ± 5° C. After addition, the content was stirred for 1 hr at 20 ± 5° C. To this mixture was slowly added |
| 26.05 g | of Lithium Carbonate. After the addition the mixture was stirred for 30 min. The mixture was subject to vacuum distillation at bath temperature 50° C. (pot temperature 37° C.) till about 150 g of liquid was collected. To 3/5 portion of above residual content was added |
| 60 g | of water. The mixture was stirred for 30 min at bath temperature 50° C. (pot temperature 47° C.), then cooled to 20° C. over 1 hr and held for at least 30 min. To the slurry was added slowly a mixture of |
| 30 g | of 2-Propanol and |
| 120 g | of water over 1 hr. The mixture was then further cooled to ca. 0–5° C. and aged for at least 2 hrs. The solid was filtered, washed with 2 × 36 g = |
| 72 g | of water, and dried under high vacuum at 40° C. for 24 hrs to afford 38.27 g (60.2% yield from L-ribose) of pure beta-1,2,3,5-tetra-O-acetyl-L-ribofuranoses as white solid. |

EXAMPLE 4

| Preparation of pure alpha-1,2,3,5-tetra-O-acetyl-L-ribofuranose | | |
|---|---|---|
|  |  | The mother liquor obtained after the precipitation of pure beta-1,2,3,5-tetra-O-acetyl-L-ribofuranose was extracted with 2X100 mL = |
| 200 | mL | of 3:7 mixed solvents of EtOAc/TBME. The combined organic layers were concentrated to almost dryness. The residue was subjected to a azeotropic distillation with |
| 20 | mL | of toluene to remove residual water. The resulting mixture (13 g) was a colorless oil that contained a 3:1 mixture of α/β-1,2,3,5-tetra-O-acetyl-L-ribofuranoses. Part of the mixture (12 g) was subjected to a flash column chromatography (140 g silica gel), eluting with a mixed solvents of EtOAc/petroleum ether (9:31), to give of |
| 4.8 | g | alpha-1,2,3,5-tetra-O-acetyl-L-ribofuranose (97.1% area purity by GC analysis) as a colorless oil. |

EXAMPLE 5

Preparation of methyl 1-(2,3,5-tri-O-acetyl-beta-L-ribofuranosyl)-1,2,4-triazole-3-carboxylate from alpha-1,2,3,5-tetra-O-acetyl-L-ribofuranose

| Preparation of methyl 1-(2,3,5-tri-O-acetyl-beta-L-ribofuranosyl)-1,2,4-triazole-3-carboxylate from alpha-1,2,3,5-tetra-O-acetyl-L-ribofuranose | |
|---|---|
|  | A 250 mL flask was charged with |
| 1.92 g | of triazolemethylester and a solution of |
| 4.8 g | of pure alpha-1,2,3,5-tetra-O-acetyl-L-ribofuranose, prepared in Example 4 in |
| 50 mL | of methyl acetate. The mixture was concentrated at atmospheric pressure to almost dryness (bath temperature, 90° C.). To this muxture was added a solution of |
| 22.7 mg | of triflic acid in 1 mL of methyl acetate. The mixture was stirred at 115 ± 5° C. (pot temperature) under vacuum (30 mbar) for 4 h. Upon completion of the reaction the mixture was cooled to 70° C. and to it was added |
| 23 mL | of 2B alcohol (ethyl alcohol). When a homogenous solution was formed the mixture was cooled to 50° C. and held until heavy precipitation formed. The mixture was then slowly cooled to −5° C. (bath temperature) in 2 h and held 13 h. The solid was filtered, washed with |

-continued

| Preparation of methyl 1-(2,3,5-tri-O-acetyl-beta-L-ribofuranosyl)-1,2,4-triazole-3-carboxylate from alpha-1,2,3,5-tetra-O-acetyl-L-ribofuranose |
|---|
| 20 mL of cold 2B Alcohol (ethyl alcohol), and dried under vacuum at 50° C. for 17 h to give 4.1 g (70% yield) of methyl 1-(2,3,5-tri-O-acetyl-beta-L-ribofuranosyl)-1,2,4-triazole-3-carboxylate as an off-white solid. |

Upon reading the present specification various alternative embodiments will become obvious to the skilled artisan. These variations are to be considered within the scope and spirit of the subject invention, which is only to be limited by the claims that follow and their equivalents.

What is claimed is:

1. A method of producing a carboxylate compound of the formula:

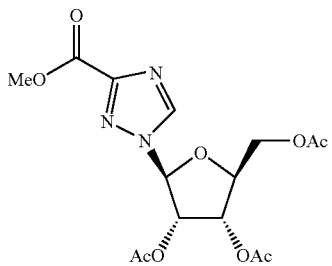

from a tetraacetyl compound of the formula:

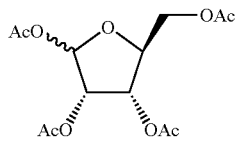

wherein said tetraacetyl compound contains at least 10 mole % of the α-anomer of the formula:

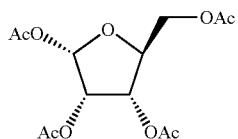

comprising reacting said tetraacetyl compound with a traazolmethyl compound of the formula:

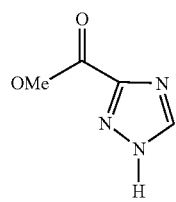

to produce said carboxylate.

2. The method of claim 1, wherein said tetraacetyl compound of the formula

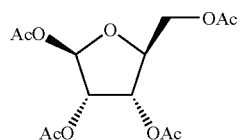

is a mixture of the α- and β-anomers wherein the mole ratio of the β-anomer to the α-anomer is from about 2:1 to about 3:1.

3. The method of claim 1, when the tetraacetyl compound is the α-anomer substantially free of the corresponding β-anomer.

4. A method of producing a carboxylate compound of the formula:

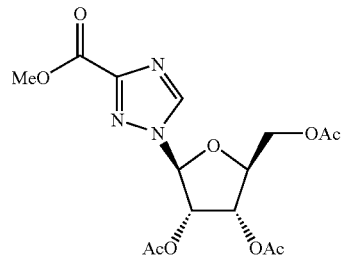

from an acetal having the formula:

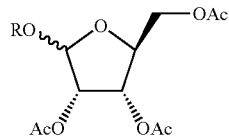

comprising hydrolizing said acetal in an acetic acid reaction medium containing acetic anhydrate to produce a tetraacetyl compound of the formula:

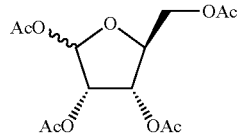

and reacting said tetraacetyl compound in said reaction medium with a traazolmetyl compound of the formula to produce said carboxylate:

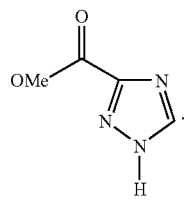

5. The method of claim 4, wherein said tetraacetyl compound is a mixture of the α-anomer and the β-anomer wherein the mole ratio of the α-anomer to the β-anomer is from about 2:1 to about 3:1.

6. The method of claim 5, wherein the tetraacetyl compound is α-anomer substantially free of the corresponding β-anomer.

* * * * *

UNITED STATES PATENT AND TRADEMARK OFFICE
CERTIFICATE OF CORRECTION

| | |
|---|---|
| PATENT NO. | : 7,034,161 B2 |
| APPLICATION NO. | : 10/638740 |
| DATED | : April 25, 2006 |
| INVENTOR(S) | : Zhiming Dong et al. |

It is certified that error appears in the above-identified patent and that said Letters Patent is hereby corrected as shown below:

Title Page:
"Item (60) Provisional application No. 60/402,780…" should be
--Item (60) Provisional application No. 60/402,788…--

Signed and Sealed this

Twelfth Day of December, 2006

JON W. DUDAS
*Director of the United States Patent and Trademark Office*